US006277067B1

(12) United States Patent
Blair

(10) Patent No.: US 6,277,067 B1
(45) Date of Patent: *Aug. 21, 2001

(54) METHOD AND PORTABLE COLPOSCOPE USEFUL IN CERVICAL CANCER DETECTION

(76) Inventor: Kerry L. Blair, 15390 Monrovia St., Overland Park, KS (US) 66219

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/832,944

(22) Filed: Apr. 4, 1997

(51) Int. Cl.$^7$ .................................................. A61B 1/06
(52) U.S. Cl. .................................... 600/167; 600/160
(58) Field of Search ............................... 600/135, 167, 600/160, 105, 109, 476; 348/68, 71, 77

(56) References Cited

U.S. PATENT DOCUMENTS

| 3,805,596 | 4/1974 | Klahr . |
| 4,300,570 | 11/1981 | Stafl . |
| 4,407,290 | 10/1983 | Wilber . |
| 4,519,684 | 5/1985 | Francis, Jr. et al. . |

(List continued on next page.)

OTHER PUBLICATIONS

Emma Gilmour, M.D., "Measuring Cervical Ectopy: Direct Visual Assessment Versus Computerized Planimetry", *American Journal of Obstetrics & Gynecology*, vol. 176, No. 1, 1977, pp. 108–111.

Paola M. Cristoforoni, M.D., "Computerized Colposcopy Results of a Pilot Study and Analysis of Its Clinical Relevances", *Obstetrics & Gynecology*; vol. 85, No. 6, Jun. 1995, pp. 1011–1016.

M.I. Shafi, "Digital Imaging Colposcopy, Image Analysis and Quantification of the Colposcopic Image", *British Journal of Obstetrics and Gynecology*, vol. 101, Mar. 1994, pp. 234–238.

L. Stewart Massad, "Use of Speculoscopy in the Evaluation of Women with Atypical Papanicolaou Smears", *The Journal of Reproductive Medicine*, vol. 38, No. 3, Mar. 1993, pp. 163–169.

W. Mann, "Papanicolaou Smear Screening Augmented by a Magnified Chemiluminescent Exam", *International Federation of Gynecology and Obstetrics*, vol. 43, 1993, pp. 289–296.

W.P. Soutter, "Computerization of a Colposcopy Clinic", *British Journal of Obstetrics and Gynecology*, vol. 98, Aug. 1991, pp. 824–828.

William E. Crisp, M.D., "The Computerized Digital Imaging Colposcope: Future Directions", *American Journal of Obstetrics and Gynecology*, vol. 162, No. 6, Jun. 1990, pp. 1491–1498.

Vittorio Contini, "Colposcopy and Computer Graphics: A New Method?", *American Journal of Obstetrics and Gynecology*, vol. 160, No. 3, Mar. 1989, pp. 535–538.

*Colposcopes & Accessories*, Leisegang Medical Inc.

*Applying Digital Processing Methods in the Analysis of Refinal Structure*, Sunanda Mitra.

*How Computer Displays Work*, Computer Display Systems.

*Applied Image Processing*, pp. 32–56.

Primary Examiner—Paul J. Hirsch
(74) *Attorney, Agent, or Firm*—Lathrop & Gage, LC

(57) ABSTRACT

A method and portable apparatus for the visual examination and grading of cervical epithelium by means of a hand-held colposcopy assembly capable of producing a digital image of the cervix. The present invention enables real-time imaging and archiving of images of the entire cervix for the purpose of detecting cancerous and pre-cancerous tissue and by virtue of computerized image processing suggests an objective diagnosis of the cervical epithelium by means of a low cost, portable, hand-held digital colposcope.

10 Claims, 10 Drawing Sheets

U.S. PATENT DOCUMENTS

| | | |
|---|---|---|
| 4,588,294 | 5/1986 | Siegmund . |
| 4,841,555 | 6/1989 | Doi et al. . |
| 4,860,371 | 8/1989 | Matsuyama et al. . |
| 4,888,490 | 12/1989 | Bass et al. . |
| 4,905,670 | 3/1990 | Adair . |
| 4,993,404 * | 2/1991 | Lane ..................................... 600/109 |
| 5,026,368 | 6/1991 | Adair . |
| 5,036,853 | 8/1991 | Jeffcoat et al. . |
| 5,179,938 | 1/1993 | Lonky . |
| 5,211,938 | 5/1993 | Kennedy et al. . |
| 5,214,456 | 5/1993 | Gersten . |
| 5,251,025 * | 10/1993 | Cooper et al. ........................ 600/160 |
| 5,251,613 | 10/1993 | Adair . |
| 5,309,214 | 5/1994 | Hashimoto . |
| 5,329,938 | 7/1994 | Lonky . |
| 5,351,676 * | 10/1994 | Putman ................................ 600/109 |
| 5,386,819 * | 2/1995 | Kaneko et al. ...................... 600/160 |
| 5,413,108 | 5/1995 | Alfano . |
| 5,421,339 | 6/1995 | Ramanujam et al. . |
| 5,450,857 | 9/1995 | Garfield . |
| 5,554,160 | 9/1996 | Caillouette . |
| 5,575,757 * | 11/1996 | Kennedy et al. .................... 600/167 |
| 5,608,451 * | 3/1997 | Konno et al. ........................ 600/109 |
| 5,654,750 * | 8/1997 | Weil et al. ............................. 348/77 |
| 5,662,584 * | 9/1997 | Hori et al. ............................ 600/167 |
| 5,701,904 * | 12/1997 | Simmons et al. ..................... 348/77 |

* cited by examiner

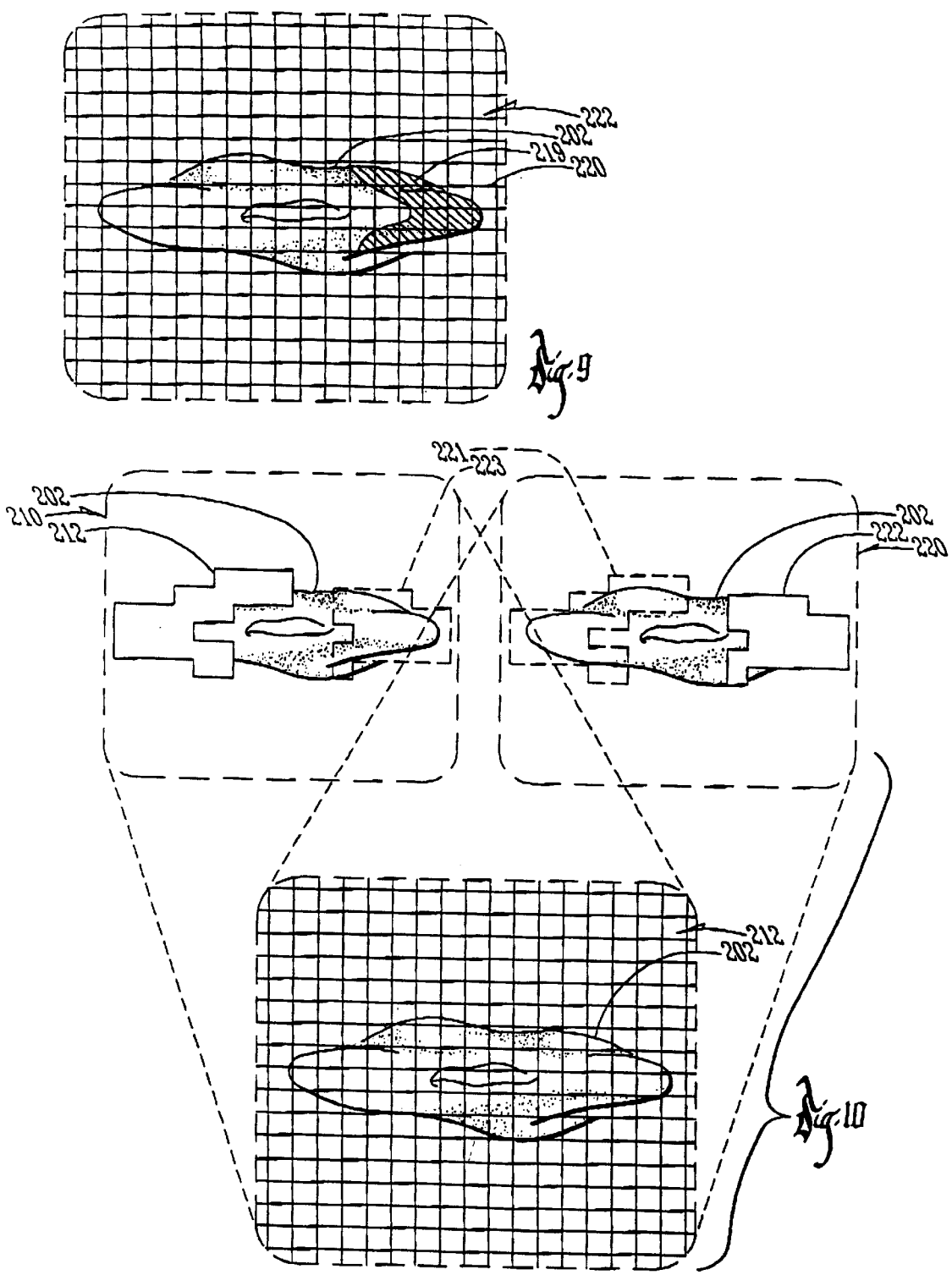

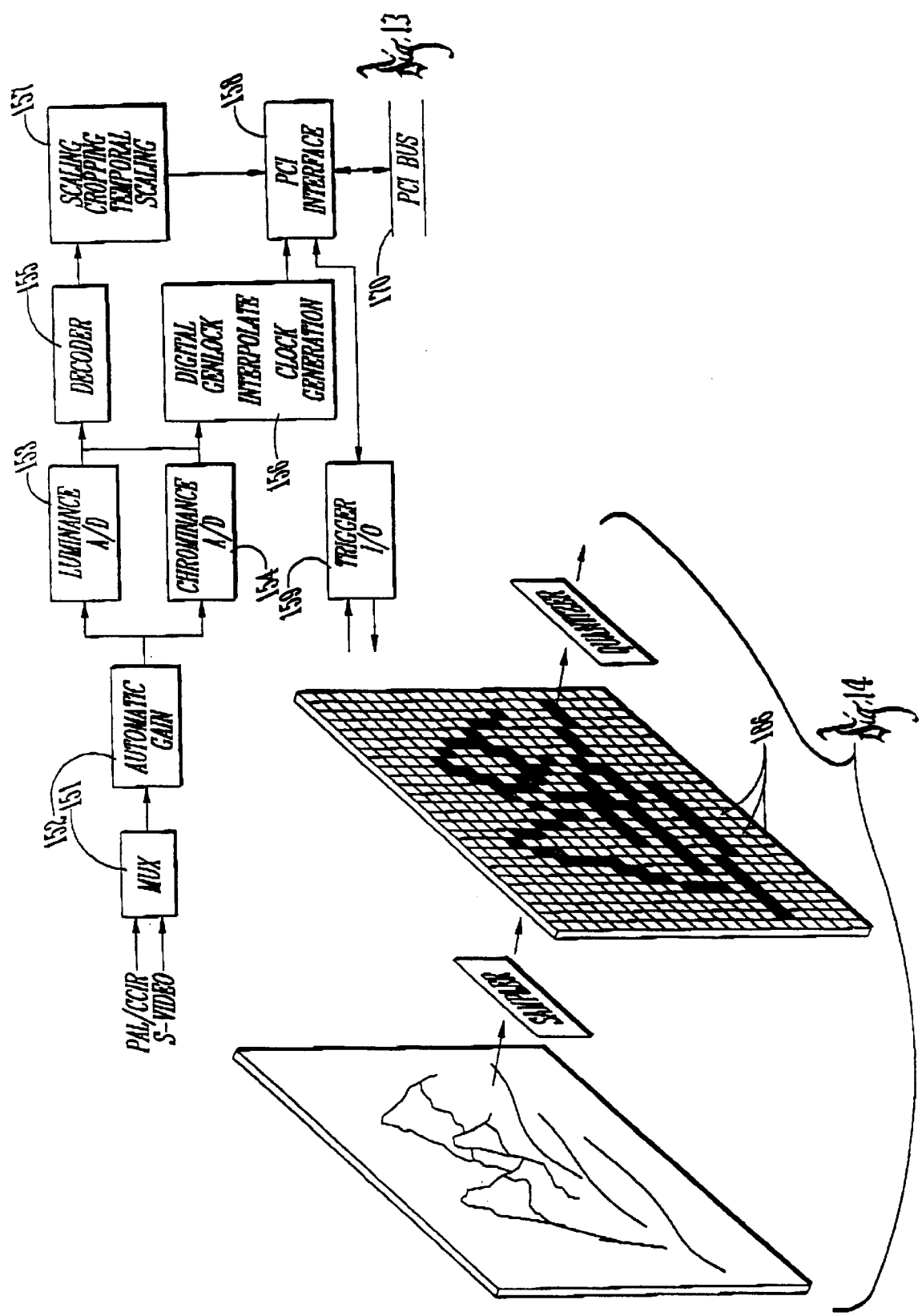

METHOD AND PORTABLE COLPOSCOPE USEFUL IN CERVICAL CANCER DETECTION

1. BACKGROUND OF THE INVENTION

1.1 Field of the Invention

The present invention relates generally to the detection of cervical cancer, and more particularly, to a method and portable apparatus for the visual examination and grading of cervical epithelium by means of a hand-held colposcopy assembly capable of producing a digital image of the cervix.

1.2 Problems in the Art

1.2.1 General Setting of the Invention

Two methods are used for early detection of cervical cancer and precancer: cytology and colposcopy. Cytology is a screening method that is practical and economical and colposcopy is a diagnostic method directed to the clinical diagnosis of patients with abnormal cytology.

1.2.2 Conventional Methods and Systems.

Over the last fifty years, Papanicolaou Smear ("Pap Smear") has become the principal cytology screening method and the cornerstone of efforts to reduce cervical cancer mortality. Pap Smear screening is effective in identifying the later stages of cervical cancer. Current estimates are that 60–70 million Pap Smears are done in the U.S. each year. Pap Smear screening has, thus, become the standard screening method for the detection of cervical cancer.

When conducting Pap Smear screenings, the gynecologist collects exfoliated cells from the surface of the cervix and places them on slides that are sent to cytologists for further examination. Cytologists then review the cells placed on the slides and look for abnormal cells. If abnormal cells are found, the Pap Smear is considered to be positive. If no abnormal cells are found, the Pap Smear is considered to be negative. In some cases, the Pap Smear slides cannot be properly evaluated by the cytologist because of technical problems associated with the Pap Smear collection process such as inadequate cell count, improper slide fixation, etc.

In the early stages of cervical disease, abnormal cell exfoliation is slow and most abnormal cells are located below the surface or are trapped by a keratin barrier covering the cervical surface. In these circumstances, the Pap Smear screening process is a relatively insensitive indicator of cervical health due to inaccessibility of abnormal cells that are otherwise indicators of cancerous or pre-cancerous tissue. HPV virus is the most common cause of keratin barriers hindering exfoliation and a significant portion of the U.S. population is known to harbor the HPV virus. This complicates the challenge of abnormal cell collection in the Pap Smear procedure.

Because of a variety of problems associated with Pap Smear screening, it is well known that the Pap Smear procedure has a high false negative and a low but statistically significant false positive rate. Studies indicate that Pap Smear screenings will fail to detect from 50%–80% of low grade cancerous lesions and even 15%–30% of high grade cancerous lesions. Repeating the Pap screening on a regular basis helps to improve on this failure to detect, but still misses an unacceptable level of diseased patients. 40% of cervical cancers occur in women who have had reasonable Pap screening. Nevertheless, in spite of its cancer detection shortcomings, Pap Smear screening is generally recognized as a practical and economical procedure for the early detection of cervical cancer.

While the Pap Smear process is designed for initial screening, colposcopy and related procedures are generally used to confirm Pap Smear abnormalities and to grade cancerous lesions. Conventional colposcopy is a subjective visual assessment of the cervix and the quality of this assessment depends greatly on the expertise of the practitioner. Since its introduction in 1925, colposcopy has acquired wide recognition as the standard follow-up clinical procedure for patients identified by Pap Smear screening as having possible cervical abnormalities. It is generally recognized that colposcopy is highly effective in evaluating patients with abnormal Pap Smears and has therefore become the standard of medical care in the Western world for this circumstance. It is estimated that approximately 4 million colposcopy examinations are currently performed in the U.S. each year.

The simultaneous use of cytology and colposcopy is potentially the most effective screening method for cervical cancer detection. The use of present-day colposcopes, however, requires special expertise, is time consuming and costly, and thus, effectively precludes its use as a standard screening method. The typical colposcope weighs between 35 and 80 pounds necessitating that it be movable (e.g., through wheels) or be permanently placed in a room. It requires time to set up as the binocular lens system and base must be positioned and oriented to aim at the exposed uterine cervix. Once oriented, the cervix must be actively visualized through the optics to insure the cervical tissue is in focus.

Although use of a colposcope as a diagnostic method for cancer detection is potentially highly effective, colposcopy is not widely used because of the special expertise required for use and interpretation of visual information collected.

1.2.3 Conventional Portable Colposcopy Assemblies

Attempts have been made to overcome the problems referenced above as associated with the use of colposcopy as a screening method. For instance, U.S. Pat. No. 4,300,570 to Stafl and U.S. Pat. No. 4,519,684 to Francis, et al. disclose a diagnostic screening method using a portable photocolposcope operable to create photographs of cervical tissue. The photocolposcope includes a single lens reflex camera equipped with an extender and a telelens which is mounted on the extender. The photocolposcope is operable to create photographs that may be converted into slide photographs of the cervix. The slide photographs are then projected onto a screen for visual evaluation by individuals having an expertise in cervical cancer screening and diagnosis. Because photographs are produced by the photocolposcope (i.e., a photograph capable of taking photographs) and its associated method, many of the limitations associated with conventional colposcopy are avoided. More particularly, the photocolposcope and method may be effectively used by persons lacking the extensive skill and training otherwise required for proper operation of conventional colposcopes and data interpretation.

Although an improvement, the photocolposcope and its associated method, disclosed in the '570 and '684 patents, suffer from a number of other problems. The effectiveness of a colposcopic photocolposcopic evaluation is highly dependant upon the image clarity since cancer diagnosis is dependant upon effective examination of tissue color, surface texture (i.e., roughness, smoothness), tissue borders (i.e., borderline between the lesion and the normal epithelium) and vascularity (i.e., capillary pattern, intercapillary density and distance). At the time a colpophotograph is created, the operator does not receive instant feedback and thus cannot be aware of problems resulting from any number of clinical or technical defects inherent in use of a photocolposcope. For example, an appreciable percentage of photographs created by photocolposcopes are defective for clinical reasons because of mucus or foreign objects obscuring the field of vision, or because a lesion may not fully be included in the field and for technical reasons because of the presence of undesirable reflective glare, inadvertent over or under exposures, and processing problems typically associated with conventional photography (including chemical and paper quality and age degradations). Yet further, the delay associated with the photocolposcopic processing method implies that: (i) the attending physician can never "see and treat" the patient; and (ii) subsequent patient examinations are often required when developed colpophotograph are later found to contain defects. Finally, although photographs are sent to experts for review and interpretation, subjective analysis of the colpophotographs still occurs and experts reviewing the photographs have only limited access to source information.

1.2.4 Conventional Computerized Colposcopy

The recent emergence of computer-aided colposcopy creates a potential for the enhancement of colposcopic assessments. Computer-aided colposcopy provides for expanded utility in digital colposcopic photography and videography, and in the management of information generated by the colposcopic examination, including computer-aided processing and enhancement of colposcopic-generated images. Computer-aided colposcopes are able to analyze images instantaneously and, under the guidance of an experienced operator suggest an objective diagnosis with a degree of accuracy beyond what experienced colposcopic operators obtained using traditional methods. Computer-aided colposcopy also sets up a platform that will facilitate the emergence and development of "telemedicine" by permitting the communication of diagnostic digital image information across telecommunication networks. See, for example, Cristoforoni, M.D., Gerbaldo, M.D., Perino, M.D., Piccoli, M.D., and Capitanio, M.D., *Computerized Colposcopy: Results of a Piolot Study and Analysis of Its Clinical Relevance*, Obstetrics & Gynecology, Vol. 85, No. 6, (June 1995); Contini, M.D., Zobbi, M.D., Pasquinucci, M.D., *Colposcopy and Computer Graphic: A New Method?*, AM J Obstet Gynecol (1989); Shafi, Dunn, Chenoy, Buxton, Williams, Luesley, *Digital Imaging Colposcopy, Image Analysis and Quantification of the Colposcopic Image*, British Journal of Obestrics and Gynecology, Vol. 101, pp. 234–238, (March 1994); Mikhail, M.D., Merkatz, M.D., and Romney, M.D., *Clinical Usefulness of Computerized Colposcopy: Image Analysis and Conservative Management of Mild Dysplasia*, Obstetrics & Gynecology, Vol. 80, No. 1 (July 1992).

Computerized colposcopy, while capable of generating, storing and manipulating image data for the production of high-quality images, is likewise suffering certain technical difficulties. Equipment size, cost, and complexity considerations create disincentives against the use of computerized colposcopy. Further, like film photography-aided colposcopy, a difficulty encountered with computer assisted digital colposcopy is reflective glare resulting from the reflection of colposcopic illumination from wet cervical tissue and its associated derogatory effect on visualized and digitally captured image quality. Technical difficulties resulting from reflective glare have been reported in the literature as responsible for significant percentages of computer-aided colposcopic captured images rendered unreadable.

A two-fold need, therefore, exists in the area of cervical-cancer detection. A simple, low-cost, portable, hand-held colposcope and colposcopic technique are needed for use in conjunction with or in place of the conventional Pap Smear procedure to improve the overall statistical accuracy of screening efforts. In addition, traditional colposcopy should be easier to perform by reducing the subjectivity of the examination and should further be capable of producing archivable images that are devoid of technical flaws and inadequacies and are readily available for subsequent exams.

2. OBJECTS, FEATURES AND ADVANTAGES OF THE INVENTION

In accordance with the present invention, a portable, hand-held colposcopic apparatus and method are disclosed for use by the physician or physician's aid in the detection of cervical cancer. The present invention enables real-time imaging and archiving of images of the entire cervix for the purpose of detecting cancerous and pre-cancerous tissue and by virtue of computerized image processing suggests an objective diagnosis of the cervical epithelium by means of a low cost, portable, hand-held digital colposcope. The apparatus and method also provide for image processing, for purposes including: (i) image enhancement to permit visualization of tissue texture, borders, color and vascularity; and (ii) reflective glare removal from digital images created.

Thus, an object of the present invention is to provide a relatively inexpensive hand-held colposcopic apparatus for use in the screening of cervical cancer or precancer.

Another object of the invention is to allow a moderately trained health care professional a rapid, computer aided means to screen a population for the presence of cervical cancer and pre-cancers.

Another object of the present invention is to provide instant feedback to the health care professional regarding the quality of the image or screening attempt.

Another object of the present invention is to provide immediate visual feedback to the health care provider to allow a more informed judgment to be made as to a treatment plan.

Another object of the present invention is to allow for enhanced patient education through the use of permanently stored "typical" images representative of common colposcopic ailments so that they may be shown to the patient and discussed at the time of the screening visit or subsequent gynecological exam.

Another object of the invention is to provide for single hand operation.

Another object of the present invention is to provide a means with which to sufficiently illuminate the vaginal cavity for tertiary naked eye viewing, precluding the need for illumination from other source.

Another object of the present invention is to provide a means with which to rapidly acquire the optimal focal distance to the target tissue without having to come in contact with tissue potentially contaminated tissue or having to view the target through the system's optics, and having to view a computer generated image of the target.

Another object of the present invention is to provide a means with which to rapidly center the target tissue in the center of the imaging system's field of view.

Another object of the present invention is to provide a means with which to allow software to reorient a displayed image to correct for device handling orientation error.

Another object of the invention is to provide a digital colposcope having non-invasive, digital camera capability that provides digital image processing such as reflective glare removal and general image enhancement, documentation, and an image archival means.

Another object of the invention is to provide a unique light source for illumination of the cervical tissue during digital image generation.

Another object of the invention is to provide a computer interface capability between the digital colposcope and a computerized digital image archival system.

Another object of the invention is to provide such a digital colposcope with improved screening and diagnostic capability, and which is useful to grade lesion severity that may be otherwise obstructed by glare.

These and other objects of the invention are attained by the invention disclosed below.

3. SUMMARY OF THE INVENTION

According to the invention, a portable, hand held, cervical-cancer detection apparatus comprises a digital camera having fixed-focus optics, a strobe illumination assembly, computer video display, processor, and housing configured to contain each of these components within a portable, hand held closure. The apparatus and associated method may be employed to create instantaneous digital images of cervical tissue for immediate viewing and digital image processing. More particularly, digital images created by the apparatus and method may be instantaneously processed to remove reflective glare or to perform any number of digital image enhancement operations for determination of tissue texture, tissue and lesion borders, and tissue vascularity, among other things.

The fixed-focus assembly includes first and second light sources that are attached to the apparatus and spaced from the optical axis of the camera. The light sources are co-planar with the optical axis and operable to emit first and second energy beams, which produce first and second spots upon contacting cervical tissue of a patient. The first and second light sources are oriented so that the first and second energy beams intersect on the optical axis at the optimum focal plane of the camera, whereby as the apparatus is aimed at cervical tissue of the patient, the first and second spots converge at the focal point of the camera, and are observed as a single dot on the tissue thereby insuring that the cervical tissue is properly focused in the camera.

The strobe light assembly, in cooperation with the digital camera and fixed focus assembly is operable to create digital composite images substantially free from reflective glare. The portable hand held cervical detection apparatus is configured with various computer peripherals, including voice recorder, wireless transceiver, and computer user interface, all of which are operable to permit quick and accurate generation and processing of data useful in cervical cancer detection.

4. BRIEF DESCRIPTION OF THE DRAWINGS

FIGS. 6–10 are representations of cervix images produced by the apparatus;

FIG. 13 is a block diagram of a PIXCI imaging board;

FIG. 14 is a representation of a digitalization process;

5. DETAILED DESCRIPTION OF THE INVENTION

In the following description of preferred embodiments of the invention, particular reference will be made to the portable apparatus for optically imaging cervical tissue that is being analyzed for cancerous abnormalities. It will be appreciated by those skilled in the art that the present invention is not limited to such treatment, but can be applied to imaging of any mammalian tissue for the identification of cancerous and pre-cancerous abnormalities.

5.1 Overview—The Inventive Portable Colposcope.

Figure 1:
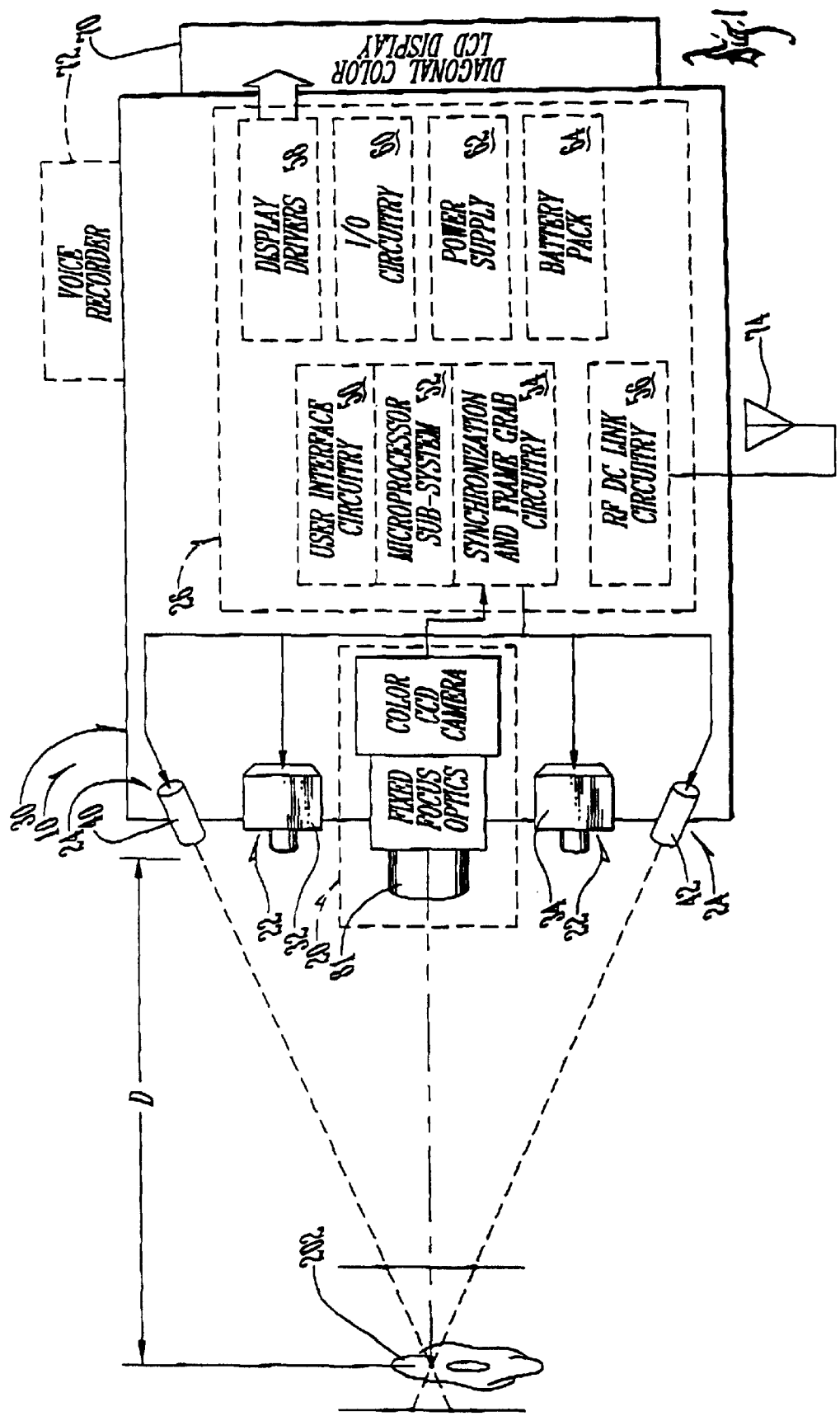
FIG. 1 is a diagram of an exemplary system designed in accordance with the present invention.

Referring first to FIG. 1, the apparatus of the invention is generally designated by the numeral 10. The apparatus 10 includes a digital imaging apparatus in the form of a digital camera 20, a strobe light assembly 22, a fixed focus laser aiming assembly 24, a processor in the form of a computer 26, computer peripherals 28, and housing assembly 30.

Digital camera 20 is of conventional design, and in the preferred embodiment, is a CooperSurgical brand HS4000 brand having a one-half inch CCD image sensor, CCD chip size of 4.6 mm. (H)×4.8 mm (V), picture elements: 768 (H) by 494 (V) or 752 (H) by 582 (V), a 2:1interlaced scanning system, a 1.5 Lux/F 1.2 (3200k) minimum illumination, 500 TV lines resolution, better than 45 db (AGC OFF) signal to noise ratio, a power supply DC 12V/250 mA, a C/CS lens mount, dimensions: 50.5 (W)×50.5 (H) ×145 (D) mn, wt=450 g. and has the following connectors: video-VMC or via 9 pin D-SUB plug; power-DC-JAK or via 9 pin D SUB plug; auto iris: 4 pin mini jack; and ext. sync-9 pin D-SUB plug. Digital camera 20 may also be any digital camera suitable for the purposes disclosed herein.

Camera 20 includes a lens mount, image sensor opening, CCD chip, video output port, and camera input port. In the preferred embodiment, camera 20 employs a single CCD chip for image creation when processing. The invention, however, may be practiced with a camera making use of multiple CCD chips.

Camera 20 includes fixed focus optics, preferably in the form of a optical glass or plastic objective lens, with appropriate focal length, field of view, and focal depth for the purposes set forth herein. Camera 20 preferably has a field of view of not less than 6 cm in diameter, focal length of 23 cm, and depth of focus to be no less than 3 cm., thus, any subject between 21.5 cm and 24.5 cm distance in front of the lens will be in focus to the CCD sensor.

Referring to FIG. 1, strobe light assembly 22 includes a first strobe light 32 and second strobe light 34.

Fixed focus laser assembly 24 include a first light emitter 40 and a second light emitter 42. Each light emitter activates to generate emitted light visible to the human eye when seen against human tissue. First and second light emitters 40 and 42 each include a partial diffusion filter suitably coupled to the light emitter through which the emitted light must pass. Partial diffusion filter consist of a translucent member with a center breach which acts as a limiting aperature. The translucent member scatters a portion of the emitted light so as to softly illuminate the field of view. The center breach is sufficiently small to allow light output to pass, preferably creating a 2 mm to 4mm light spot on any object placed in the optical path of the light emitter. The spot of light is then visible by an operator. In the preferred embodiment, the light emitter is a laser diode (Hitachi HL6720G) with a 670 nm wavelength, an output of up to 5 mW, with a raw beam diameter of 1.5 mm with 6 degree divergence, and suitable input ports. It should be noted that other types of light emitters could be used in a similar fashion with or without the partial diffusion filter. If non laser or non coherent light is used, the center breach would be supplanted with a lens to focus the emitted light passing through it. In the practice of the present invention, this light would need to be focused onto a small enough area to appear on the target subject as a bright point of light within the diffusely illuminated field. Further, it shall be understood that any mechanism that easily locates the cervix at the focal point of the camera is an equivalent of the present laser assembly 24.

The first light emitter 40, and partial diffusion filter is suitably attached to the apparatus 10 so as to border the objective lens, and is oriented in such a way as to project its output to cross the field of view of the objective lens. Emitter 40 is oriented so that the output through the center breach intersects a specific point in space in front of the objective lens. The specific point in space is determined by two factors, the focal distance of the objective lens, and the field of view of the objective lens. The preferred focal distance is 23 cm and the preferred field of view at this distance be 6 cm in diameter. The specific point in space is the center of the field of view of the objective lens at the focal distance.

The second light emitter 42 and partial diffusion filter is attached to apparatus 10 in the same fashion as emitter 40. However, the second light emitter 42 and partial diffusion filter are located at some distance from first light emitter 40. In the present embodiment, emitter 42 it is located on the side of the objective lens opposite that on which emitter 40 is attached. The emitters 40 and 42 are configured and oriented so that the point of light from the first light emitter 40 and the point of light from the second light emitter 42 are distinguishable as separate points of light when the distance between apparatus 10 and the target subject is greater that 23.5 cm. Similarly, the point of light from the first light emitter 40 and the point of light from the second light emitter 42 are distinguishable as separate points of light when the distance between the apparatus and the target subject is less the 22.5. In the preferred embodiment, the distance between the two light emitters, 40 and 42, is set to be between 3.5 cm and 7.5 cm. By being oriented and configured in this fashion, if the optical path of the light emitter is obstructed the field of view of the objective lens is likely obstructed. Because the primary target subject of the present invention is in a cavity, knowing that the field of view is being obscured is of significant importance.

Computer 26 is a miniaturized personal computer design and has, in the preferred embodiment, the following processing features: a 99Mhz Advanced Micro Devices ELAN400SC microprocessor, 16Mbytes of RAM memory, and a color Liquid Crystal Display (LCD) with color output capability. For the purposes of disclosing the invention, however, computer 26 is disclosed in terms of user interface circuitry 50 (in the form of hardware buttons and software activating icons), microprocessor sub-system 52, synchronization and frame grab circuitry 54, RF DC link circuitry 56, display driver 58, IO circuitry 60, power supply 62, and battery pack 64. It is understood, however, that computer 26 may comprise other features and functionalities that are well known to be associated with personal computers. Computer 26 is of a size and configuration so that it may be physically located within housing 30 and operably connected to the various components of apparatus 10 to achieve the purposes disclosed herein.

Peripherals 28 include a miniature color LCD display monitor 71, microphone 72, audio output 74 (to include an appropriately sized speaker with frequency response of 4,000 to 15,000 Hz, up to 65 db output intensity, with appropriate ports for signal input and volume output control), a wireless receiver and transmitter 74 (the transmitter is preferably in the form of a radio spread spectrum transmitter operating a 900 MHz to 2.4 GHZ). Other conventional computer peripherals may be added as desired. It should be understood that the monitor 71 and other preipherals may comprise other features that are well known to be associated with personal computers, especially lap top computers.

A roll axis sensor in the form of an earth gravity directional detector may also optionally be included. Such a sensor may be desirable because the uterine cervix has no visual reference of its own which may be used to indicate posterior and anterior. The roll axis sensor is configured to give the apparatus user a visual reference to this orientation. Each time an image is captured, an electronic signal is sent by the roll axis sensor for use by the computer 26 to present a visual reference indicating anterior and posterior. Alternatively, such a signal can be used by the computer 26 to alter the displayed image to orient the image to correct for error incurred when the image was captured. Housing 30 comprises a housing of any suitable material of construction and configuration to operatively contain, in a portable configuration, the digital camera 20, strobe light assembly 22, fixed focus lazer assembly 24, computer 26, and peripherals 28 for use as shown and described herein. The apparatus 10 is considered portable because the entire apparatus weighs less than 10 pounds, and preferably between 3 to 5 lbs. Moreover, the entire apparatus has a displaceable volume of approximately 600 in.$^3$, and can be stored easily on a shelf in a doctor's office (approximately 1100 in.$^3$). The apparatus 10 is preferably free from any cables, cords or other tehters that impair the attending physician's freedom of movement. It will be understood that the use of such cables and cords in conjunction with the apparatus 10 is within the scope of the present invention. Portability is a key aspect of the invention especially in light of the increasing number of female gynecologists.

Referring to FIG. 13, frame grabber circuitry 54 is designed as a personal computer peripheral card of conventional design and includes video input, control output, and data input/output. In the preferred embodiment, the data input/output bus is accomplished via an industry standard PCI bus as interfaced to a personal computer. A block diagram of a PIXCI™ frame grabber computer peripheral card is presented. The frame grabber imaging board includes a multiplexer 151, an automatic gain 152, a luminous A/D converter 153, a chrominance A/D converter 154, decoder 155, digital genlock/interpellate clock generation feature 156, a scale cropping temporal scaling feature 157, a PCI interface 158, and a trigger I/O 159. The frame grabber 40 in a preferred embodiment is an Epix Corporation, 381 Lexington Drive, Buffalo Grove, Ill. 60089, and is capable of grabbing any one or more frame of a continuous sequence of frames from video output generating frames at 30 frames per second. Frame grabber 40 also preferably includes a synchronize trigger feature, and memory buffers.

The camera 20, strobe light assembly 22, fixed forcus laser assembly 24, computer 26, and peripherals assembly 30 are operably interconnected by conventional means to perform the functions and attain the objects disclosed herein.

5.1.1 Selection of Colposcopy Optics

It will be appreciated by those skilled in the art that it will be beneficial to select colposcopy optics and strobe lighting so that regions of illumination in the digital images represent an appreciable portion of the field of view of the digital colposcope—but without creating overlapping glare regions—thus maximizing the extent to which the vaginal cavity may be illuminated with a minimum of shadows.

5.2 Operation of the Portable Colposcope.

Figure 3:
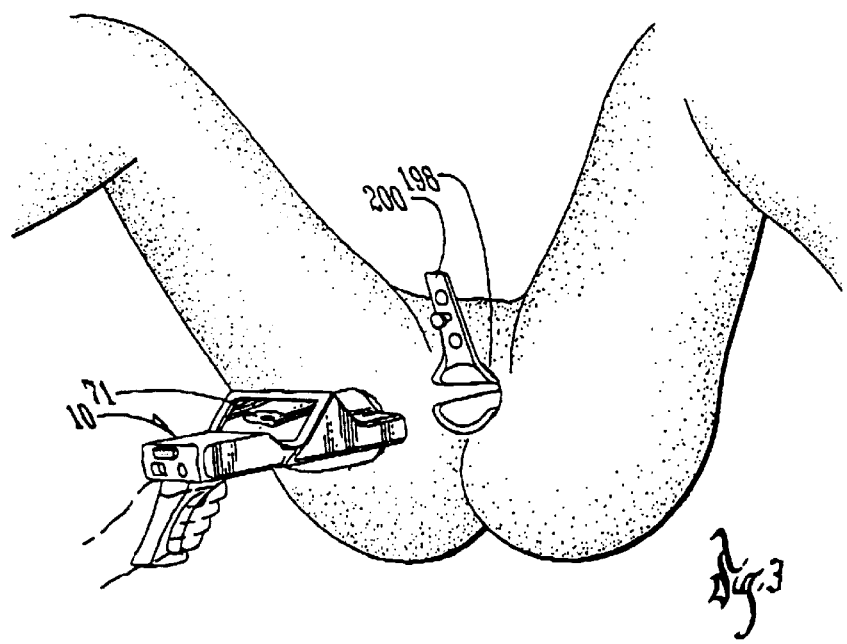
FIG. 3 is a perspective view of the apparatus of the present invention positioned for taking a photograph of the cervix.
Figure 4:
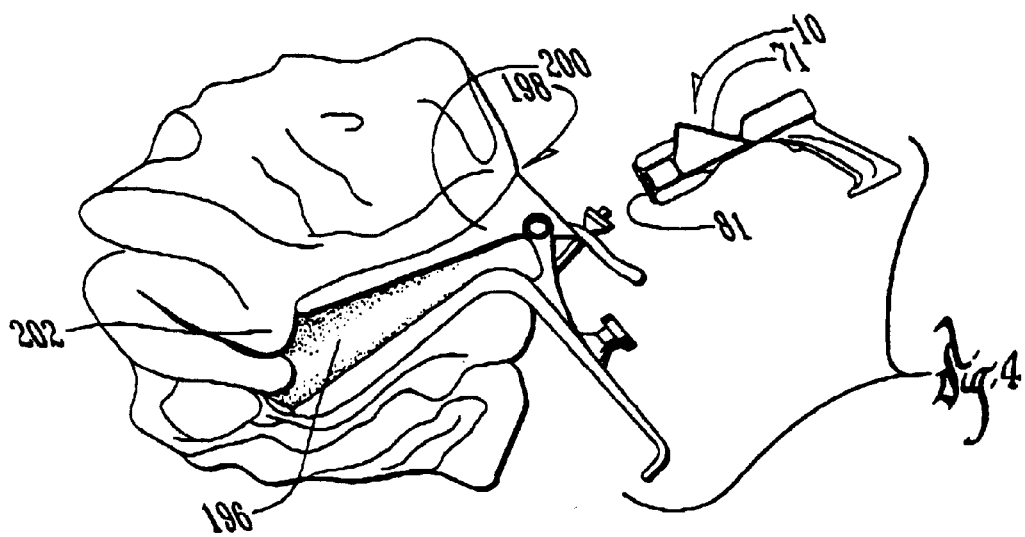
FIG. 4 is a schematic view, partially in cross-section, of the vaginal area showing the optical path of the inventive apparatus.
Figure 5:
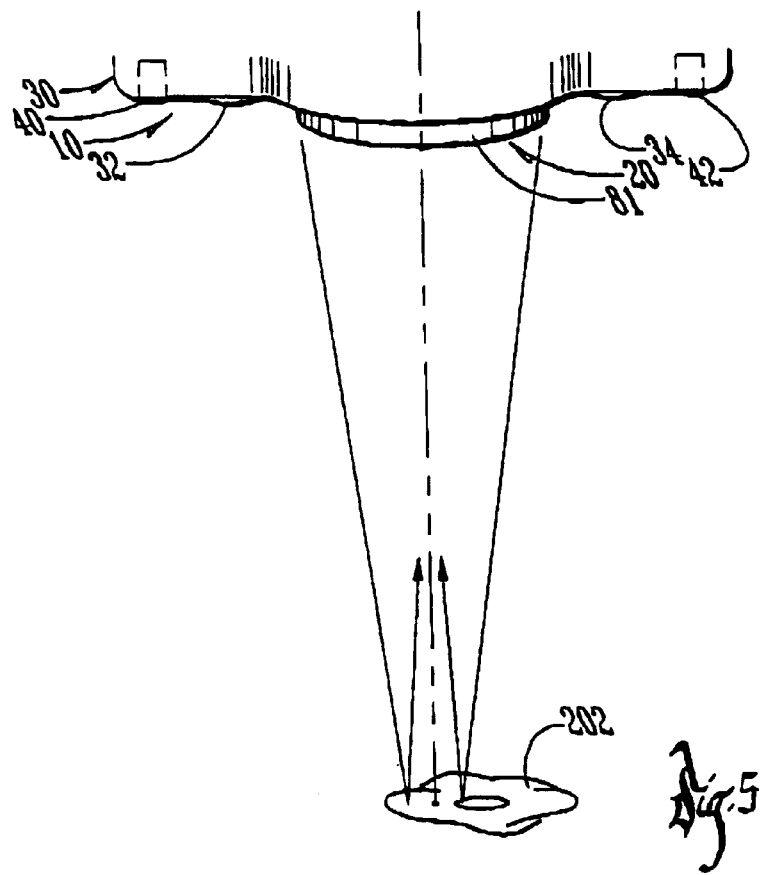
FIG. 5 is a schematic diagram of the apparatus photographing a cervix.
Figure 6:
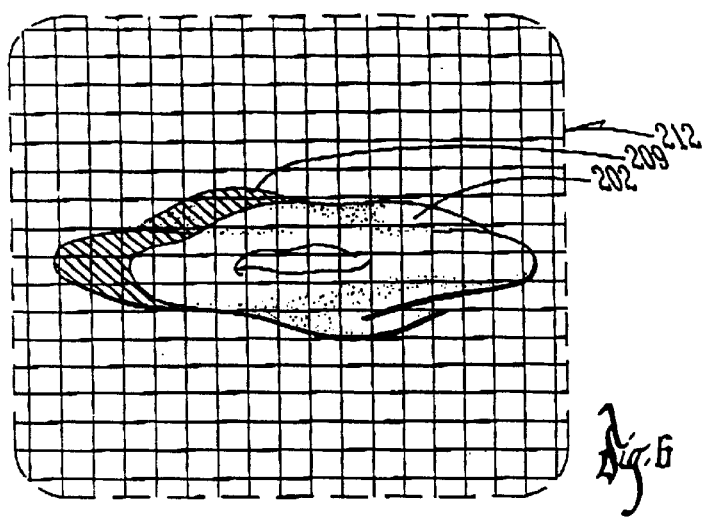
Figure 7:
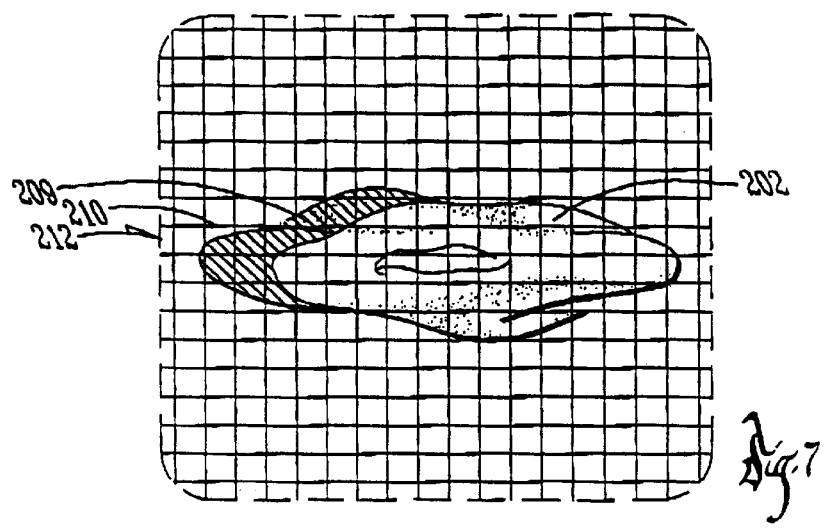
Figure 8:
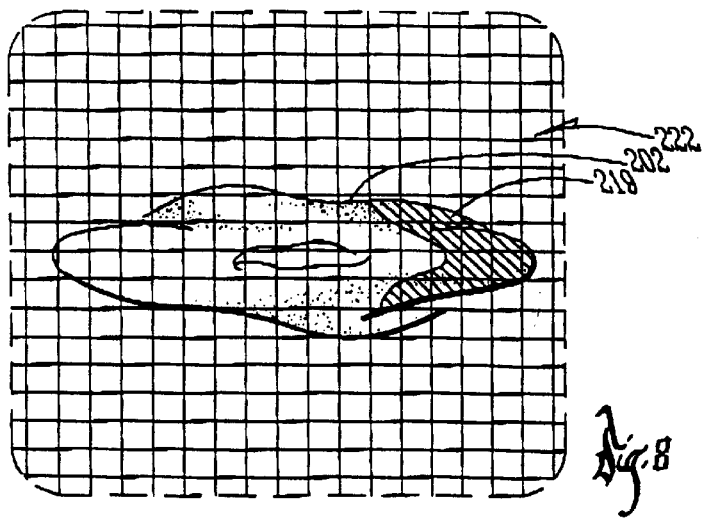
Figure 11:
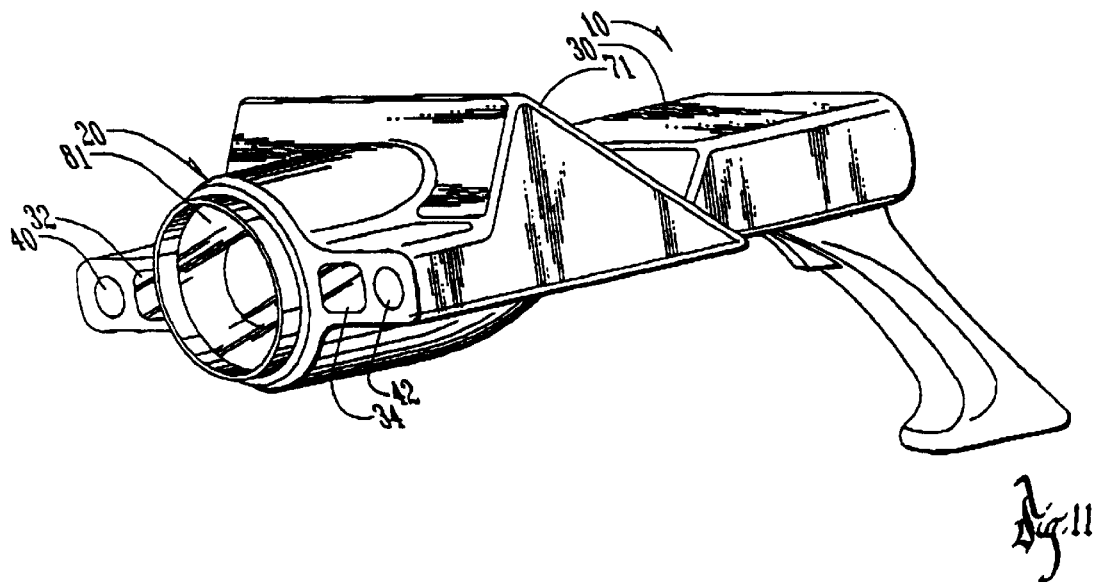
FIG. 11 is a perspective of a digital camera employed in the present invention.
Figure 12:
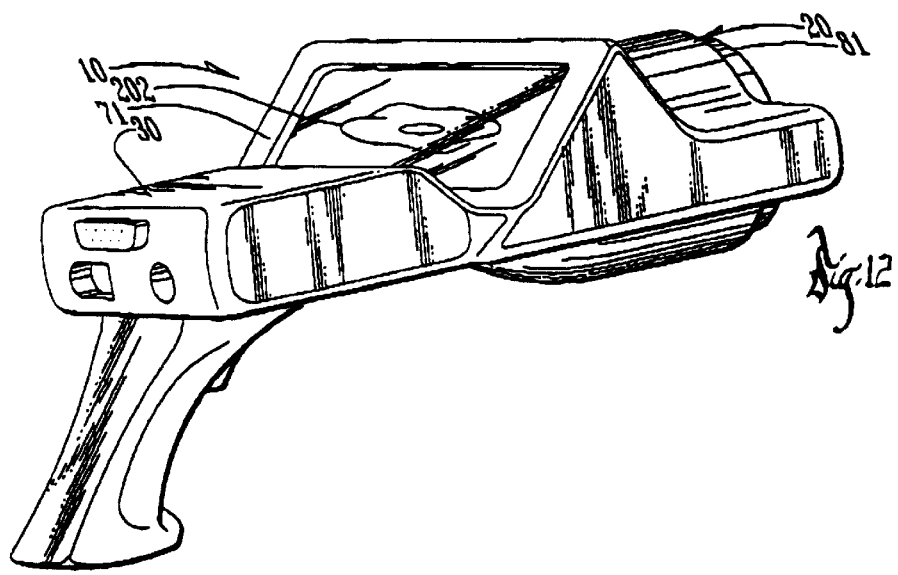
FIG. 12 is a perspective of a digital camera employed in the present invention.

In operation, apparatus 10 is used by an operator when conducting an examination of a patient lying on an appropriate exam table on her back with her legs up in stirrups, as shown in FIG. 3. A vaginal speculum 200, or similar device is inserted into the vaginal canal and locked opened to gain exposure to the cervix for viewing. While viewing the cervix it is often necessary for the operator to use one hand on the speculum 80 to position it so as to present the cervix in a position most advantageous for viewing.

When desired, the operator may flip an "On/Off" switch associated with apparatus 10 to the "On" position to permit battery pack 64 and power supply 62 to energize apparatus 10. The apparatus 10, typically held and operated by one hand, is used in two primary modes of operation: viewing mode and imaging mode.

The display monitor 71 is operable to indicate the apparatus state of readiness and is used by the operator to input commands through use of the user interface circuitry 50, in conjunction with various rocker switches and hardware buttons used singularly or in combination to activate software operating within computer 26 to effect various functionalities described herein.

Using the user interface circuitry 50, the operator begins by selecting the type of imaging test to be performed. The available choices could include; high resolution full color, low resolution full color, black and white, near infrared, and near ultraviolet, and the like, to make a selection. The operator simply uses a rocker switch and an enter button to select the desired imaging mode depicted on the display monitor 71. Display monitor 71 will then indicate that the apparatus 10 is in a "ready" state in the imaging mode. In the imaging mode, an aim/fire button associate with apparatus 10 is enabled and will activate when depressed. When not in the imaging mode, the aim-fire button is inactive.

Having selected "imaging mode," the operator directs with one hand the distal end of the apparatus generally towards the cervix while viewing the cervix with naked eye, and with the other hand manipulates the speculum in order to obtain maximum exposure of the cervix. The aim/fire button is depressed to a first position to activate the fixed focus laser assembly 24 and to deactivate the display monitor 71 (or renders it blank).

As apparatus 10 is moved to and from a target subject, the fixed focus laser assembly 24 projects two points of light that impinge upon and reflect off of any surface in the optical path of the fixed focus laser assembly 24. The operator directs the two points of light towards the cervix. The two points of light are seen to converge or diverge as the apparatus 10 is moved towards and away from the cervix. The operator directs the two points of light to converge on the relative center of the target subject. If one or both of the two points of light falls on a target other than the desired target subject, then it can be expected that the resultant image would be obscured by the unwanted target and adjustments to position must be made to gain a unobscured view of the cervix.

It will be understood and appreciated by those skilled in the arts that the cervix is the primary target subject and that it is located at the end of a tubular vaginal structure. Therefore it is important to direct an imaging system in a fashion most parallel to the center of this tubular structure in order to gain the best view of the target subject at the end of the tube. If the viewing angle of the imaging system relative to this tube is too oblique, the resultant image or view would be obscured by the proximal portion of the tube.

When the two points of light converge to form one point of light and that one point of light falls on the respective center of the cervix the apparatus 10 is in focus and aimed at the visual center of the cervix. The operator then depresses the aim/fire button to a second position initiating the image capturing sequence.

When the aim/fire button is fully depressed to its second position, the fixed focus lazer assembly 70 turns off and the strobe light assembly 22 activates. As the first strobe light 32 flashes the camera 20 captures a first image. Immediately after this a second strobe light flashes and in similar manner a second image is captured. These two images are then processed in the computer 26 and stored in the digital memory storage. Immediately, one of the images is rendered on the display 71. This signals the end of the "imaging mode". Thus, the apparatus 10 is operable to select a desired image, point and shoot and the resultant picture is immediately displayed.

The operator may then depress a glare removal button to display the image without glare. As used herein, glare is defined to mean that condition of detector/pixel saturation caused by a sufficiently high intensity of light shining on the detector. The light intensity required to illuminate the wet irregular surfaces of a vaginal cavity creates regions of glare in images produced of the vaginal cavity. In the practice of the invention, therefore, it is necessary to create at least two digital images with substantially identical fields of view but with glare, should it occur, in different regions of each image.

It will be appreciated by those skilled in the art that it will be beneficial to select colposcopy optics and strobe lighting so that regions of glare in the digital images represent an appreciable portion of the field of view of the digital—but without creating overlapping glare regions—thus maximizing the extent to which the vaginal cavity may be illuminated.

Camera 30 is operable to generate a video image output of cervix 202 that comprises the generation an output at the rate of 30 image frames per second. It will be appreciated, however, that the invention can be practiced with video outputs generated at different rates.

The video output exits camera 20 output port and is directed to frame grabber 54. Frame grabber 54 is operable to asynchronously select any of the video images created by camera 20 and generate a image signal which exits the frame grabber 54 through a data output port and is sent to a computer 26. Computer 26 is then operable to archive an image for any desirable purpose, including image enhancement, documentation, archival, or transmission to other destinations. Computer 26 is further operable to reproduce a digital image of cervix 202 on monitor 167 or in hard copy by means of reproduction of image by a printer.

At any time when not in the "imaging mode", the operator may add verbal dictation, to accompany an image produced by apparatus 10. Depressing a push to talk button for a period of time will cause the computer 26 to digitally record the audio signal it receives from the audio microphone 72. When the push to talk button is depressed, the apparatus will emit an audible beep through the use of the audio output. The beep will indicate to the operator to begin speaking to record the message. When the operator is finished speaking, the push to talk button is released. This digitized audio signal is stored by the computer 26 in digital memory storage as part of the image file. When audio information is accompanying a digital image file, an icon will appear at the lower border of the image on the display 71 to indicate the presence of audio information for that image. To hear audio information the operator will depress the push to talk button for a different prescribed time, at which time the audio recorded message is played back through the audio output means.

The operator can choose to take another image by using the display 71 and the user interface 50 to activate the apparatus 10 for imaging. The operator may also choose to discard an image and do so by using the display 71 and the user interface 50 to select the image the user wishes to discard. Once the image to be discarded is selected, depressing a discard button will delete the image from the digital memory storage.

In similar fashion the user may choose to print or archive an image. Using the display 71 and the user interface 50 the image is selected and by depressing a print button or a archive button the computer 26 will send the digital data to the wireless transmitter 74. The wireless transmitter 74 will transmit the digital file via radio waves to an appropriately equipped and activated computer server. Depending on the action selected by the operator, the digital file will be archived and or sent on to a printer for immediate printing. As an alternative to wireless, a standard serial link can transmit the images to a computer server.

When the operator is finished using apparatus 10, the on/off switch is moved to the "off" position. This completes the operation of the apparatus.

5.3 Digital Image Enhancement

Computer 26, and particularly user interface circuitry 50, is designed and configured to permit enhancement of digital images created with apparatus 10 for screening and diagnositic purposes. Conventional digital imaging enhancement techniques are employed to facilitate visualization of tissue texture, tissue and leision borderlines and tissue vascularity, all important components of cancer screening and diagnosis. Specific enhancement techniques include, but are not limited, to those disclosed. See, for example, Cristoforoni, M.D., Gerbaldo, M.D., Perino, M.D., Piccoli, M.D., and Capitanio, M.D., *Computerized Colposcopy: Results of a Piolot Study and Analysis of Its Clinical Relevance*, Obstetrics & Gynecology, Vol. 85, No. 6, (June 1995); Contini, M.D., Zobbi, M.D., Pasquinucci, M.D., *Colposcopy and Computer Graphic: A New Method?*, AM J Obstet Gynecol (1989); Shafi, Dunn, Chenoy, Buxton, Williams, Luesley, *Digital Imaging Colposcopy, Image Analysis and Quantification of the Colposcopic Image*, British Journal of Obestrics and Gynecology, Vol. 101, pp. 234–238, (March 1994); Mikhail, M.D., Merkatz, M.D., and Romney, M.D., *Clinical Usefulness of Computerized Colposcopy: Image Analysis and Conservative Management of Mild Dysplasia*, Obstetrics & Gynecology, Vol. 80, No. 1 (July 1992), all teaching of which are hereby incorporated by reference.

According to the instant invention, therefore, the advantages of highly accurate computerized colposcopy in cervical cancer detection are that screening and diagnosis may be employed in conduction with a hand-held, portable, colposcope that is relatively inexpensive and easy to use.

5.4 Creation of Glare-Free Digital Images of Vaginal Cavities

A general description of the techniques for the creation of digital images as employed by apparatus 10 will now be provided.

5.4.1 Creation of Digital Images Generally.

Processes and equipment associated with the generation of digital images are well known in the art and are described in references such as Baxes, G.A., *"Digital Image Processing,"* John Wiley & Sons (1994) (ISBN 0-471-00949-0) Awcock, G. W. and Thomas, R., *"Applied Image Processing,"* McGraw-Hill, Inc. (1995) (ISBN 0-07 001470-1); Russ, J. C., *"The Image Processing Handbook,"* CRC Press (2nd Ed. 1995) (ISBN 0-8493-2516-1).

Non-digitized images, such as conventional photographs, are comprised of continuously varying shades and colors. The shades vary from light to dark and the colors vary from red, green, to blues.

A digital image is composed of discrete levels of gray tone ("brightness"), as opposed to the continuously varying tones associated with non-digitized conventional photographs. A digital image is created from a continuous tone image by dividing it up into individual points of brightness. (See FIG. 14) Each point of brightness is converted into a digital data value. The process of digitizing an image is called "sampling," and the process of converting each discrete sampled item into a digital value is call "quantization." The sampling process samples the intensity of the continuous-tone image at specific locations. The quantization process determines the digital brightness values of each sample ranging from black, to grays, to white. The quantitized spacial sample is referred to as a picture element, or "pixel." The processes of sampling and quantization are collectively referred to as image digitization.

Figure 15:
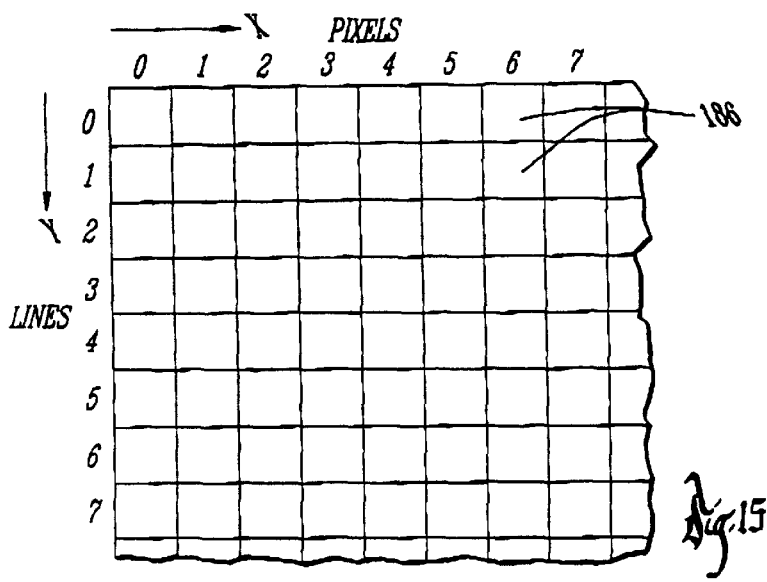
FIG. 15 is a representation of a pixel array.
Figure 16:
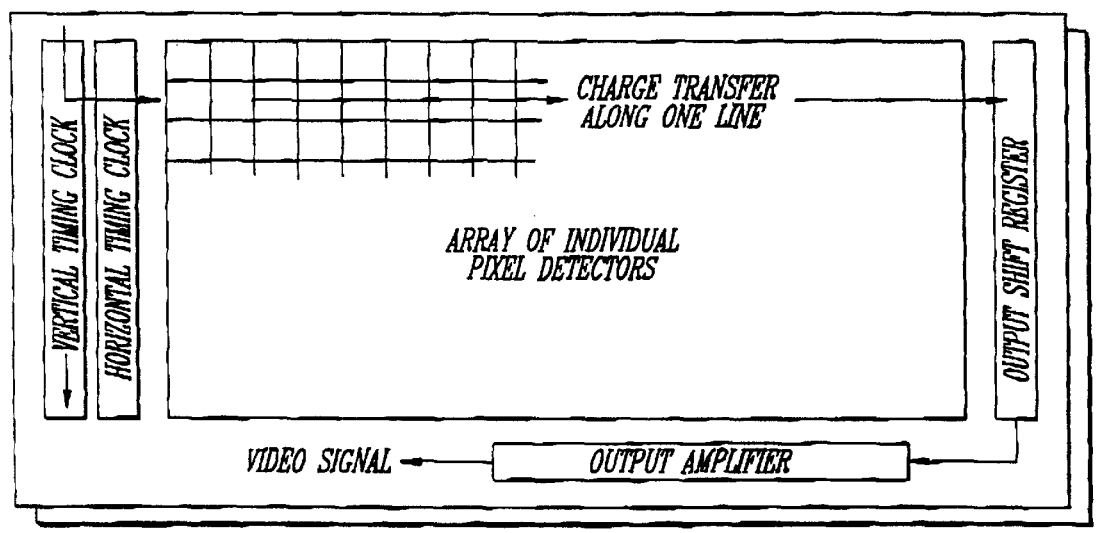
FIG. 16 is a representation of pixel charge transfer.

Referring to FIGS. 15–16, in image digitization, an image is generally sampled into a rectangular array of pixels 186. Each pixel has its own (x, y) coordinate that corresponds to its location within the rectangular array that comprises the image. Once sampled and quantitized, each pixel will have generated an output quantity that is proportional to the input lighting intensity. Image resolution is thus a function of the number of pixels that make up the rectangular array and the capability of the digital image to resolve the elements, as closely as possible, to the original scene. The pixel arrays are traditionally orthogonal (Cartesian geometry) such as that shown in FIGS. 15 and 16. Arrays, however, may also have an hexagonal configuration. See, e.g., Awcock, et al., *"Applied Image Processing,"* at 64.

With charge couple device technologies ("CCD"), it is possible to place more than 300,000 pixels in an area of less than one square centimeter. More specifically, there are 307,200 pixels in a conventional 640×480 array. Each pixel of a CCD functions as a detector of light intensity, and more specifically as a photo counter, as electrons are raised to the conduction band in an isolated well.

Referring to FIG. 16, a signal is read out from each line of detector pixels to produce an analog voltage. FIG. 16 shows a schematic diagram of a typical CCD camera chip. A vertical timing clock selects each line of pixel detectors in turn. Then a horizontal clock shifts the contents from each detector to its neighbor, causing the line to read out sequentially into a shift register and amplifier that produces an analog voltage as a function of time. Specific CCD array architectures include (a) parallel/serial; (b) interlined transfer; and (c) frame transfer.

The process previously described for the generation of digital images also applies to color images. In a single CCD chip comprised of a rectangular array of pixels capable of generating a color image, pixels in each line are constructed with filters such that every third pixel in each line detects red, blue, and green light. A single color CCD chip will be composed of detector pixels in repeating sequential groups of red, green, and blue detectors. Thus, if each detector has a gray-scale of $2^8$, it will create an analog output between 0 and 255 that is proportional to the red, green, or blue light intensity striking the particular detector. Further, each pixel consisting of a red, green, and blue detector are represented by a 24-bit word.

In digital imaging, a wide range of colors can be created by mixing red, blue, and green in various combinations, and are well developed in the art. See, e.g., Baxs, *"Digital Imaging Processing,"* at 53–56.

It will thus be appreciated that the processes described herein for monochrome digital imaging can be employed in color digital imaging by first converting the 24-bit color words in the pixel array rectangle into individual color intensity values. The conversion process applied in reverse is then used to recreate a color digital image using color intensity values.

5.4.2 Creation of Digital Images for Use in the Creation of a Glare-Free Composite.

An aspect of the invention will now be described that is associated with the use of inventive digital colposcope to create at least two images having the same field of view but which display different regions of reflective glare.

As used herein, glare is defined to mean that condition of detector/pixel saturation caused by a sufficiently high intensity of light shining on the detector. The light intensity required to illuminate the irregular surfaces of a vaginal cavity often creates regions of glare in digital images produced of the vaginal cavity. In the practice of the invention, therefore, it is necessary to create at least two digital images with substantially identical fields of view but with glare, should it occur, in different regions of each image.

Figure 2:
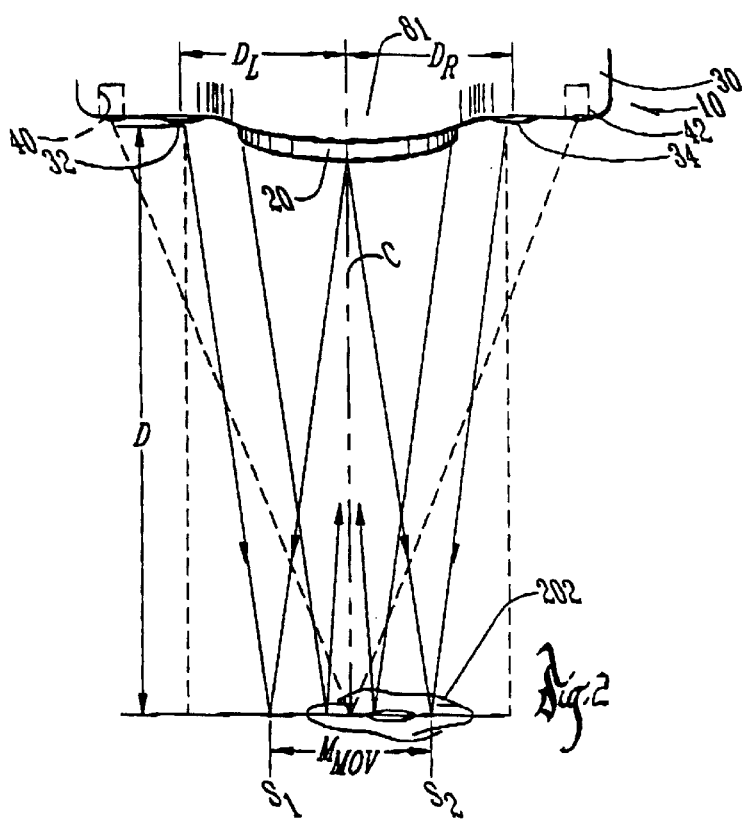
FIG. 2 is a diagram illustrating the optical path of the colposcopic and the strobe light assembly.

The inventive technique and equipment used for this purpose is schematically illustrated in FIG. 2. A apparatus 10 is positioned between first and second strobes 32, 34, separated by a distance $D_L$ and $D_R$, respectively. If strobes 32, 34 are oriented such that their light paths reflect from the surface and back into the optical path c of lens of camera 20, as shown in FIG. 2, regions of glare will be created at locations $S_1$ and $S_2$ on the surface. (The exact shape of the glare regions created will depend upon the surface contour, surface conditions—wet or dry, and light intensity.) The distance $M_{mov}$ that separates the center of the glare regions is a geometric function of distances $D_L$ and $D_R$. Thus, to insure that the glare region created by strobe 32 does not overlap with glare region created by strobe 34, at a given light intensity, the position of the strobes need merely be separated by a sufficient distance.

The same concept applies to the illumination of the vaginal cavity. That is, when the apparatus 10 is oriented for viewing of the vaginal cavity so that the cervix is within its field of view, strobes 32, 34 should be separated by sufficient distance so that any glare regions created by each strobe light does not overlap in the digital image, but not so far separated so as to have an obscured view of the cervix.

5.4.3 Detailed Operation of Strobe Light Assembly

Referring now to FIGS. 2, 6–11, strobes 32, 34 are separated from camera 20 by distance $D_L$, $D_R$, respectively, so that a glare region 210 (FIG. 7) appearing in a first digital image 212 created with illumination by strobe 32 s a location in the image different from a glare region 220 (FIG. 9) appearing in a second digital image 222 created with illumination by strobe 34 Although it is preferable in the practice of the invention to create images with non-overlapping glare regions, it will be understood by those skilled in the art that the invention has glare-removal utility even when glare regions overlap.

As described above, frame grabber 54 operably connected to camera 20 and a strobe controller (of conventional design) so that frame grabber 54 signals strobe controller to cause strobes 32, 34 to emit pulses of light to illuminate cervix 202 for the creation of first and second digital images 212, 222 (FIGS. 6–9). To achieve this purpose, trigger I/O 159 of frame grabber 54 provides input signals to strobe input ports of strobe lights 32, 34, respectively. Input signals are passed from ports to trigger gate inputs TRIG1, 2, shown in FIG. 18.

Figure 18:
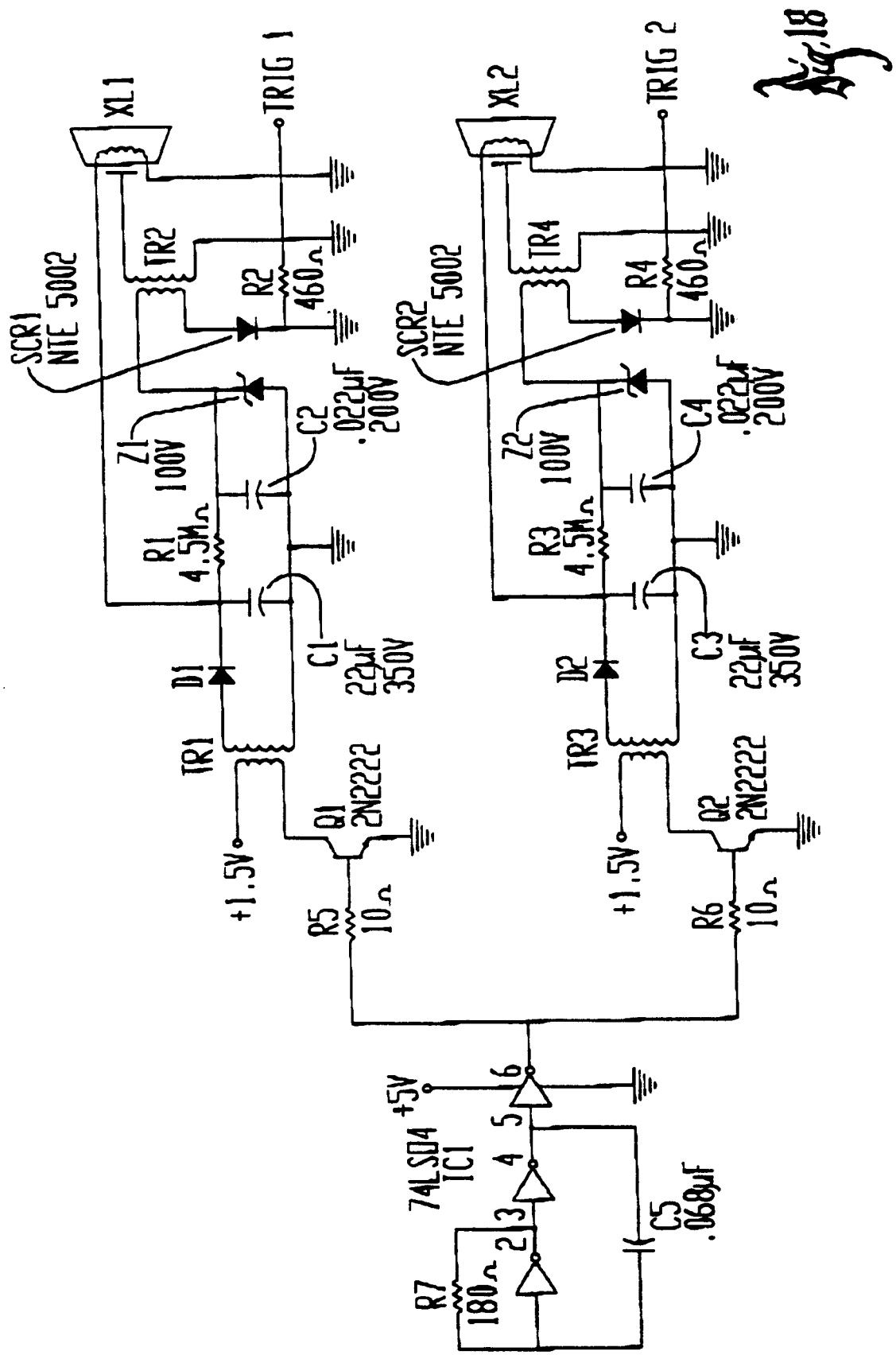
FIG. 18 is an electrical schematic of strobe light assembly circuit.

Referring now to a strobe circuit schematically shown in FIG. 18, a xenon flash board provides the circuitry necessary to precharge and then flash either of the two xenon flash tubes upon prescribed trigger inputs. Xenon is chosen as the preferred discharge gas in the flash tube because of its extremely high luminance (i.e., brightness) versus halogen or normal incandescent flash tubes.

The circuit illustrated by FIG. 18 functions as follows: IC1, R7 and C5 constitute an oscillator circuit which runs at a frequency of 60 hertz at 0 to +5 volts. The oscillator output (IC1, Pin6) drives transistor Q1 on then off in oscillatory fashion inducing a collector current which pulses voltages between +0.3 volts and +1.5 volts on the primary side of transformer TR1. Transformer TR1 has a high secondary to primary winding ratio and thus functions as a voltage amplifier. The secondary windings of TR1, together with dio Dl, chop and amplify the voltage pulses induced from the primary of TR1 so that a voltage of +300 volts is developed across the positive terminal of electolidic capacitor C1. This +300 volts is also connected to the anode (positive) side of the xenon flash tube XL1 (which adjoins light emission port associated with strobe 32). The cathode (negative) side of the flash tube is connected to ground, thus an arc discharge voltage of 300 volts is presented across the terminals of the flash tube. Current limiting resister R1 reverse biases zener diode Z1 to its break down voltage of 100 volts so that in conjunction with capacitor C2, a regulated voltage of +100 volts is presented to the primary side of trigger transformer TR2 and thus the anode of the trigger switch SCR1. In order to trigger the flash circuit, a positive going (TTL level) pulse is presented to the gate of the trigger switch SCR1. This turns SCR1 on, thus creating a voltage spike of approximately +100 volts on the primary side of the trigger transformer TR2. TR2 has a high secondary to primary winding ratio so that it also acts as a voltage amplifier, thus creating a secondary voltage pulse of approximately +1,000 volts in response to the trigger pulse. This 1,000 volt pulse is applied to the trigger electrode of the xenon flash tube which, together with the +300 volt anode to cathode voltage, causes the xenon gas in the flash tube to ionize and then discharge completely as the voltage charge of electrolidic capacitor C1 is effectively shorted to ground through the flash tube. Xenon flash tube XL2 (which adjoins light emission port associated with strobe 34) works effectively the same way with its own set of corresponding circuitry.

It will be appreciated, however, that other circuits or means may be employed to operate the strobe lights so that the strobe lights are operably coupled to the digital camera 20 and operate to emit pulses of light from two separate locations in a synchronized fashion so that a first pulse of light illuminates an object when a first image is created and second pulse of light illuminates an object when a second image is created.

5.4.4 Creation of Glare-Free Digital Image Composite—The Algorithm

Digital images 212, 220 are archived by computer 26 for processing. While the following description is directed to glare removal by processing of only two images, it will be appreciated by those skilled in the art that digital image glare removal, according to the invention, may be practiced by processing more than two images.

Figure 17:
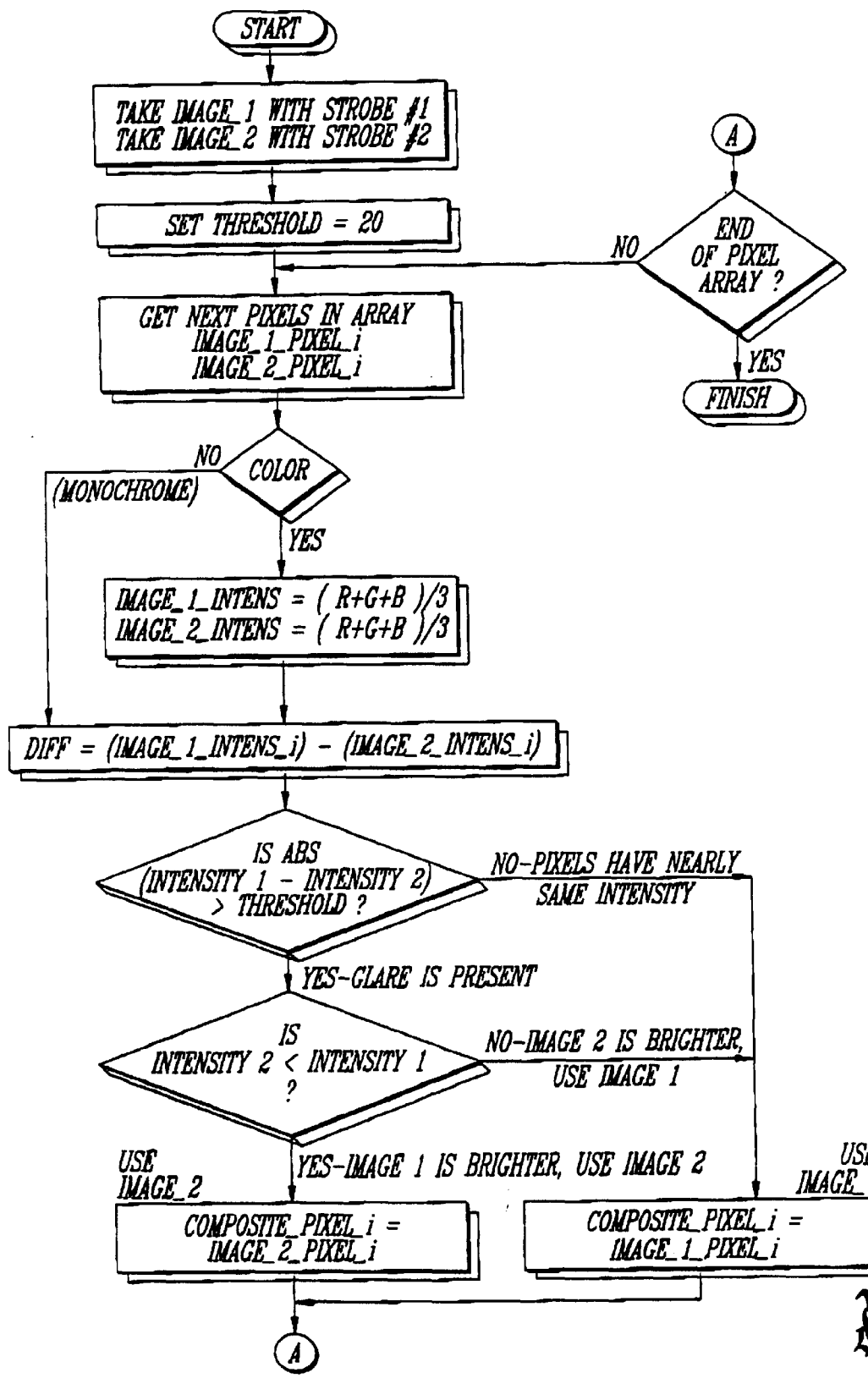
FIG. 17 is a flow chart depicting the software logic used to detect glare.

By way of example, there is illustrated in FIG. 17 a flow chart that describes the algorithm by which a glare-free composite image 230 can be generated by computer 26 through processing of images 212, 220.

When desired, an operator can initiate the following sequence which is manually initiated by trigger means (not shown) associated with frame grabber 54.

Upon initiation, frame grabber 54 takes first image 212 which has been illuminated by strobe 32 from the video output of camera 20. Next, frame grabber 54 takes image 220 which has been illuminated by strobe 34 from camera 20 video output. Images 212 and 220 are immediately archived by computer 26.

An arbitrary glare threshold value is entered into the computer 26 which will be used to determine whether glare is present. A processing means, e.g., software or hardware, compares each pixel in the array associated with first image 212 to its corresponding pixel in second image 220. A difference is calculated by subtracting from the value associated with a pixel from first image 212 the value associated with the corresponding pixel in image 220. If the difference is greater than zero—indicating that the image 212 pixel is brighter than the corresponding pixel in image 220, the processing means will select the pixel from image 212 for use in the composite image 230. If the difference is less than zero—indicating that the pixel associated with image 212 is brighter—the processing means will compare the difference to the threshold value. If the difference is not greater than the threshold value—indicating that no glare is present, the processing means selects the pixel associated with first image 212 for use in the composite image 230.

If the difference is equal to or greater than the threshold value—indicating a glare condition, the processing means will select the pixel from second image 220 for use in creating composite image 230. The processing means will in this way cycle through a comparison of all pixels in both images to create composite 230. Composite 230 will then be archived by computer 50 for any desired use, including display on monitor 71, or printout on a printer. With the algorithm, the computer 26 is operable to identify pixels associated with first glare region 210 (FIG. 7) caused by glare 209 and second glare region 220 associated with glare 219.

Referring to FIG. 10, a composite image is shown as being produced by removing glare region 220 from first digital image 212 and replacing it with non-glare region 221 from second digital image 220. Conversely, a composite image may be created by removing glare region 222 from second digital image 220 and replacing it with non-glare region 223 from first digital image 212. The teachings and technique of all references cited herein, including patent and literature references, are incorporated herein by reference.

It will be appreciated that the apparatus described above may be employed as an in situ cancer-detection technique directed to virtually any type of tissue. In fact, the portable colposcope apparatus and technique described above may generally be employed for the topological mapping of the acetowhitening affects on cervical tissue, topological mapping of cervical vascularity and other potentially cancerous tissue vascularity, topological mapping of glycogen content of cervical tissue, and measurement of cervical anatomy.

What is claimed is:

1. A portable, cervical-cancer detection apparatus comprising a camera having fixed-focus optics, an optical axis associated with the fixed-focus optics, a focal point associated with the fixed-focus optics and lying a predetermined distance from the camera, the apparatus further comprising a processor, a display monitor, and first and second light sources attached to the apparatus and spaced from said optical axis of the camera, the light sources being co-planar with said optical axis and operable to emit first and second energy beams which produce first and second spots upon contacting cervical tissue of a patient, the first and second light sources being oriented so that the first and second energy beams intersect on said optical axis at the focal point of the camera, whereby as the apparatus is aimed at cervical tissue of the patient the first and second spots converge at the focal point thereby insuring that the cervical tissue is properly focused in the camera.

2. The apparatus according to claim 1 further comprising a housing, the housing containing the camera, the processor, the monitor, and first and second light sources.

3. The apparatus according to claim 2 wherein the apparatus is hand held and weighs less than five pounds.

4. The apparatus according to claim 2, wherein the camera is a digital camera operable to create at least first and second digital images, the digital images having substantially the same field of view, each digital image comprising an array of discrete digital image elements, each image element of each image having a spatially identical corresponding element in at least the other digital image, and wherein the apparatus further comprises strobe lights associated with the camera for illuminating the cervix with light pulses emitted from at least two locations, said strobe lights being operable to synchronize the emission of the pulses so that the cervix is illuminated with said first pulse for the creation of the first image and the cervix is illuminated with the second pulse for the creation of the second image, first glare and non-glare regions created by the first pulse in the first image, second glare and non-glare regions created by the second pulse in the second image, and wherein the processor includes digital processing means operable to create a substantially glare-free digital composite image by replacing the discrete digital elements of the glare region of one image with the corresponding discrete digital elements from the non-glare region of the other image.

5. A portable, cervical-cancer detection apparatus comprising, a digital camera having fixed-focus optics, an optical axis associated with the fixed-focus optics, a focal point associated with the fixed-focus optics and lying a predetermined distance from the camera, and first and second light sources attached to the apparatus and spaced from said optical axis of the camera, the light sources being co-planar with said optical axis and operable to emit first and second energy beams which produce first and second spots upon contacting cervical tissue of a patient, the first and second light sources being oriented so that the first and second energy beams intersect on said optical axis at the focal point of the camera, whereby as the apparatus is aimed at cervical tissue of the patient the first and second spots converge at the focal point thereby insuring that the cervical tissue is properly focused in the camera.

6. The apparatus according to claim 5, wherein said camera is located between the first and second light sources.

7. The apparatus according to claim 6, wherein the first and second light sources are spaced from said optical axis of the camera such that the distance of convergence and divergence of the first and second spots on the cervical tissue of the patient is less than the distance of movement of the camera along the optical axis toward and away from the cervical tissue.

8. The apparatus according to claim 6, wherein the focal point is positioned approximately 23 cm from the camera.

9. The apparatus according to claim 8, wherein the first and second light sources is set apart between 3.5 cm and 7.5 cm.

10. The apparatus according to claim 5, wherein the apparatus is sized to be hand-held and weigh less than five pounds.

\* \* \* \* \*